United States Patent
Picchione, II

[11] Patent Number: 6,029,277
[45] Date of Patent: Feb. 29, 2000

[54] THERAPEUTIC SUPPORT GLOVE

[75] Inventor: Nicholas Picchione, II, East Greenwich, R.I.

[73] Assignee: Data Building, Inc., Warwick, R.I.

[21] Appl. No.: 09/271,781

[22] Filed: Mar. 18, 1999

[51] Int. Cl.$^7$ .................................................. A41D 19/00
[52] U.S. Cl. ...................... 2/162; 2/16; 2/161.1; 473/62; 600/15; 602/14
[58] Field of Search .................................. 2/16, 159, 160, 2/161.1, 161.2, 162, 164, 167, 170, 917; 128/878; 473/54, 60, 62; 600/9, 15; 602/9, 14, 21; 607/111

[56] References Cited

U.S. PATENT DOCUMENTS

| | | | |
|---|---|---|---|
| 4,138,108 | 2/1979 | Robinson | 273/54 |
| 4,535,482 | 8/1985 | Spector et al. . | |
| 4,543,671 | 10/1985 | Monk . | |
| 4,587,672 | 5/1986 | Madnick et al. . | |
| 4,684,123 | 8/1987 | Fabry . | |
| 4,727,602 | 3/1988 | Giese et al. . | |
| 4,759,084 | 7/1988 | Madnick et al. . | |
| 5,035,003 | 7/1991 | Rinehart . | |
| 5,139,187 | 8/1992 | Fowler | 224/151 |
| 5,187,814 | 2/1993 | Gold . | |
| 5,269,023 | 12/1993 | Ross | 2/66 |
| 5,415,624 | 5/1995 | Williams | 602/21 |
| 5,509,143 | 4/1996 | Yates et al. . | |
| 5,530,967 | 7/1996 | Cielo . | |
| 5,572,744 | 11/1996 | Reid, Jr. et al. . | |
| 5,617,583 | 4/1997 | Yates et al. . | |

*Primary Examiner*—Diana Oleksa
*Assistant Examiner*—Katherine Moran
*Attorney, Agent, or Firm*—Salter & Michaelson

[57] ABSTRACT

A therapeutic support glove for providing relief for such things as hand fatigue, carpal tunnel syndrome, arthritis, tendinitis and other known ailments associated with the human hand including a cuff portion having two pockets defining corresponding cavities at the opposite interior surfaces thereof. The pockets are positioned in opposing relation to each other so that when the glove is worn on the user's hand, one of the pockets is adjacent the outer portion of the user's wrist, and the other pocket is adjacent the inner portion of the user's wrist no matter which of the user's hand the glove is worn on. An elongated opening extends along the top edge of the pockets for insertion of a selected therapeutic pack within the pocket cavity. The arrangement is such that the therapeutic pack may preferably be positioned adjacent the inner portion of the user's wrist for implementation of the desired therapeutic process. The glove further includes a hand portion secured to the cuff portion providing means for covering the inner palm portion and back portion of the user's hand. The hand portion has openings formed therein at the terminal end thereof for insertion of the user's fingers when putting the glove on the user's hand, so that the user's fingers remain uncovered and unrestricted when the glove is in use.

8 Claims, 5 Drawing Sheets

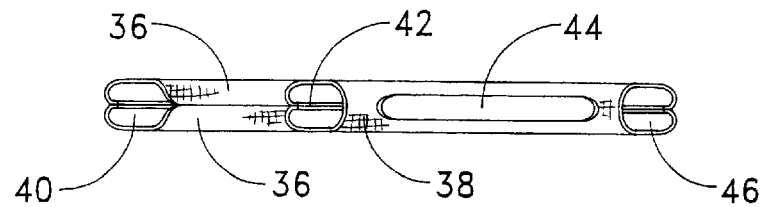
FIG. 4
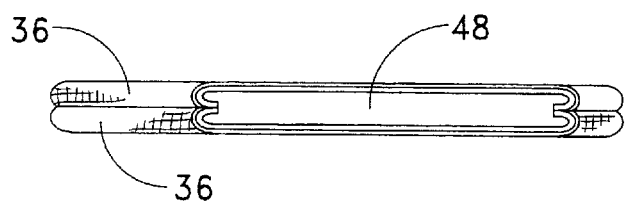
FIG. 5
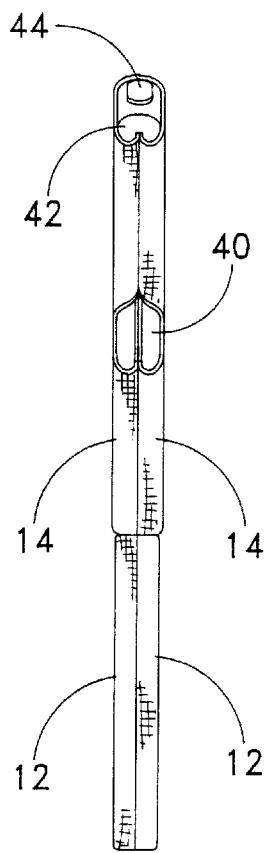 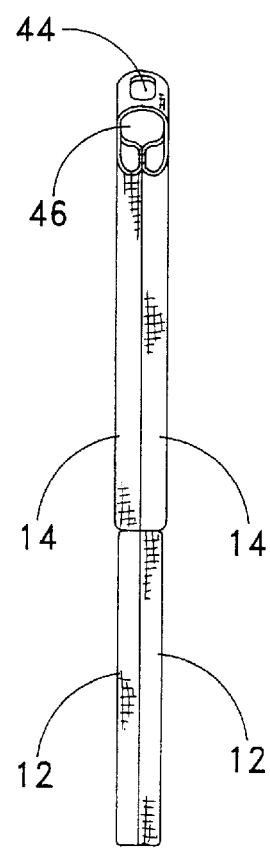
FIG. 6　　　　　　FIG. 7

THERAPEUTIC SUPPORT GLOVE

BACKGROUND AND SUMMARY OF INVENTION

This invention relates generally to gloves, and more particularly, to a therapeutic hand glove which helps produce relief from hand fatigue, carpal tunnel syndrome, arthritis, tendinitis and other uncomfortable aches and pains associated with the human hand. Specifically, the glove has pockets formed on both sides of the glove cuff for insertion of a selected heat pack, cold pack, or magnetic pack for the desirable therapeutic purpose. The dual pocket construction allows the glove to be worn on either of the user's hand wherein the inserted therapeutic pack is located adjacent the user's wrist for implementing the desired therapy.

Various types of gloves having pouches or pockets formed therein have heretofore been known in the prior art. In this regard, the majority of these type of gloves are contemplated for use in cold weather and provide varying means for distributing heat to portions of the human hand, including the fingers and finger tips. One problem traditionally associated with these type of heating gloves is the difficulty with inserting and removing varying heating elements which are retained within the cavity of the pocket incorporated into the glove. A number of gloves have pocket flaps or releasable securing means for retaining the heating element within the cavity of the pocket of the glove. However, these securing means often times provide awkward and frustrating obstacles for quickly and easily replacing and removing the heating element from the pocket of the glove. Further, these types of gloves usually have a number of layers incorporated therein for better protection against the cold outdoor winter elements.

The instant invention is directed to a therapeutic support glove for providing relief for such things as hand fatigue, carpal tunnel syndrome, arthritis, tendinitis and other known ailments associated with the human hand. The support glove comprises a cuff portion which entirely surrounds the user's wrist, and a hand portion which covers the inner palm portion and back portion of the user's hand. The cuff portion has two pockets at the interior surface of the cuff of the glove. The pockets are positioned in opposing relation to each other so that when the glove is worn on either of the user's hands, one of the pockets is always adjacent the outer portion of the user's wrist, and the other pocket is adjacent the inner portion of the user's wrist. An elongated opening extends along the top edge of the pockets for insertion of the selected therapeutic pack within the pocket cavity, so that the therapeutic pack may be positioned adjacent the inner portion of the user's wrist for implementation of the desired therapeutic process. The hand portion of the glove is stitched to the cuff portion and has openings formed therein at the opposite end thereof for insertion of the user's fingers when putting the glove on the user's hand, so that the user's fingers remain uncovered and unrestricted when the glove is in use, as is well known in the art.

Accordingly, among the several objects of the instant invention are: the provision of a therapeutic support glove which provides relief for various kinds of hand fatigue and hand ailments; the provision of a therapeutic support glove having a pair of opposing pockets formed in the interior of the cuff portion of the glove; the provision of a therapeutic support glove which includes heat packs, cold packs, or magnetic packs for insertion within one of the pockets formed in the interior of the cuff portion of the glove for implementing the desired therapeutical process; the provision of a therapeutic support glove wherein the selected therapy packs are positioned within the cuff pocket adjacent the inner portion of the user's wrist; the provision of a therapeutic support glove which may be worn on either of the user's hands while still providing a pocket adjacent the inner portion of the user's wrist; the provision of a therapeutic support glove which leaves the user's fingers uncovered and unrestricted; the provision of a therapeutic support glove which provides a snug firm fit and is neat and attractive in appearance; and the provision of a therapeutic support glove which is cost efficient and easy to manufacture.

Other objects, features and advantages of the invention shall become apparent as the description thereof proceeds when considered in connection with the accompanying illustrative drawings.

BRIEF DESCRIPTION OF THE DRAWINGS

In the drawings which illustrate the best mode presently contemplated for carrying out the present invention:

FIG. 4 is a top view thereof;

FIG. 5 is a bottom view thereof;

FIG. 6 is a left edge view thereof;

FIG. 7 is a right edge view thereof;

DETAILED DESCRIPTION OF THE PREFERRED EMBODIMENT

Figure 1:
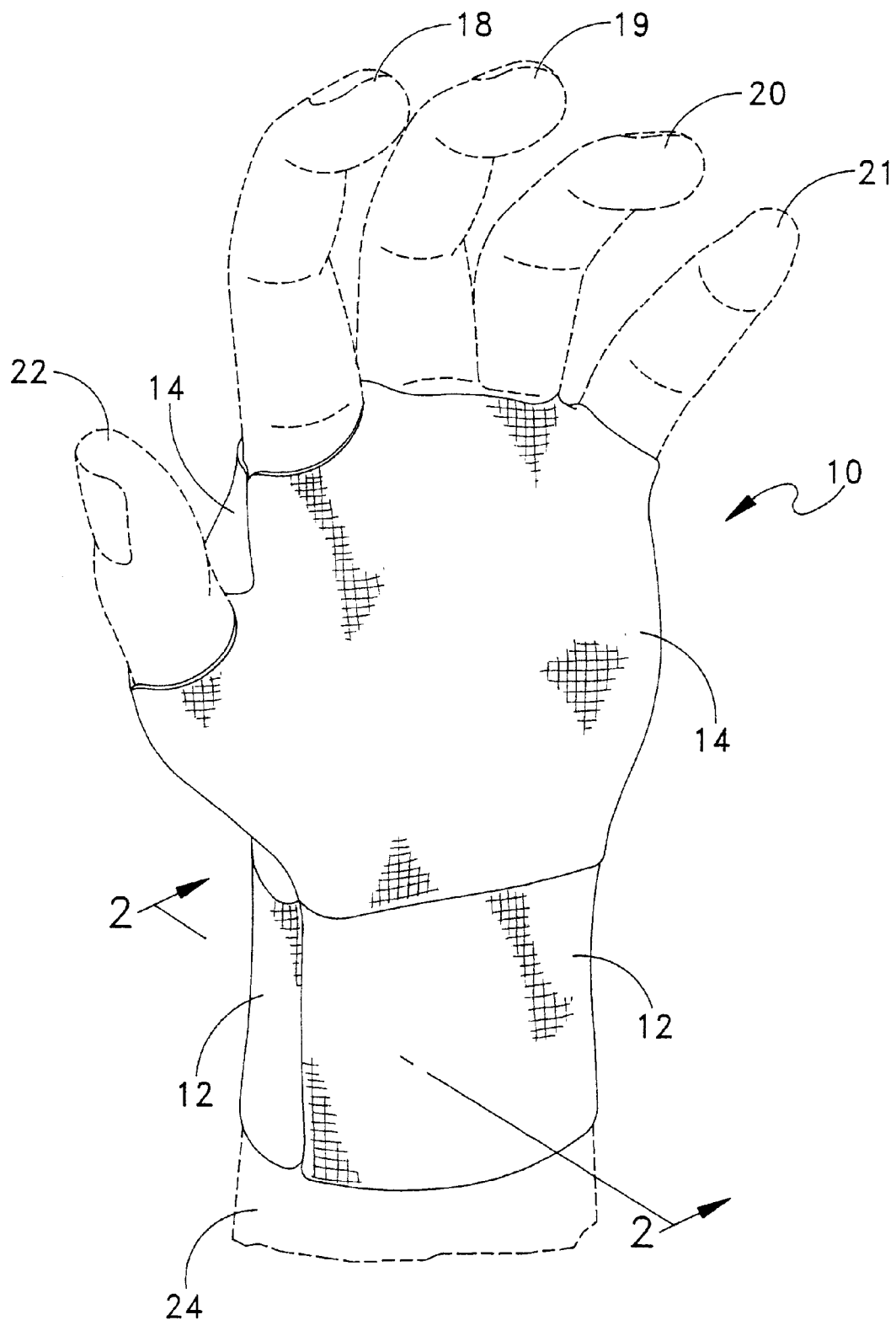
FIG. 1 is a perspective view showing the therapeutic support glove of the instant invention being worn on a user's hand.

Referring now to the drawings, and more particularly to FIG. 1, the therapeutic support glove of the instant invention is shown and generally indicated at 10. As will hereinafter be more fully described, the instant invention provides for an improved support glove and therapeutic pack assembly. The arrangement is such that the glove may be worn on either hand of the user with the selected therapeutic pack positioned adjacent the inner portion of the user's wrist for implementing the desired therapeutic process. The glove includes a cuff portion 12 and a hand portion 14. The cuff portion 12 completely surrounds the wrist 24 of the person wearing the glove 10 and has opposing pockets formed in an interior portion thereof, not shown in FIG. 1, for receiving the selected therapeutic pack 26. The hand portion 14 of the glove 10 completely covers the back and palm portions of a person's hand 16. The fingers and thumb 18–22 of the hand 16 of the user are not covered and are therefore unrestricted by the glove 10 for better feel and movement for such activities as computer typing and other continuous or repetitive hand motion activities. Both the cuff 12 and hand 14 portions of the glove 10 are fabricated from a resilient spandex-type material which helps retain body heat, and in turn, raises the blood pressure in the wrist 24, hand 16, and also the fingers 18–22 of the hand 16 of the person wearing the glove 10. The snug fitting nature of the glove 10 gives support to the flesh and muscle structure of the user's hand 16 and wrist portion 24. The stretching nature of the spandex-type material reacts to each movement of the user's hand producing an automatic massaging and energizing effect.

Figure 2:
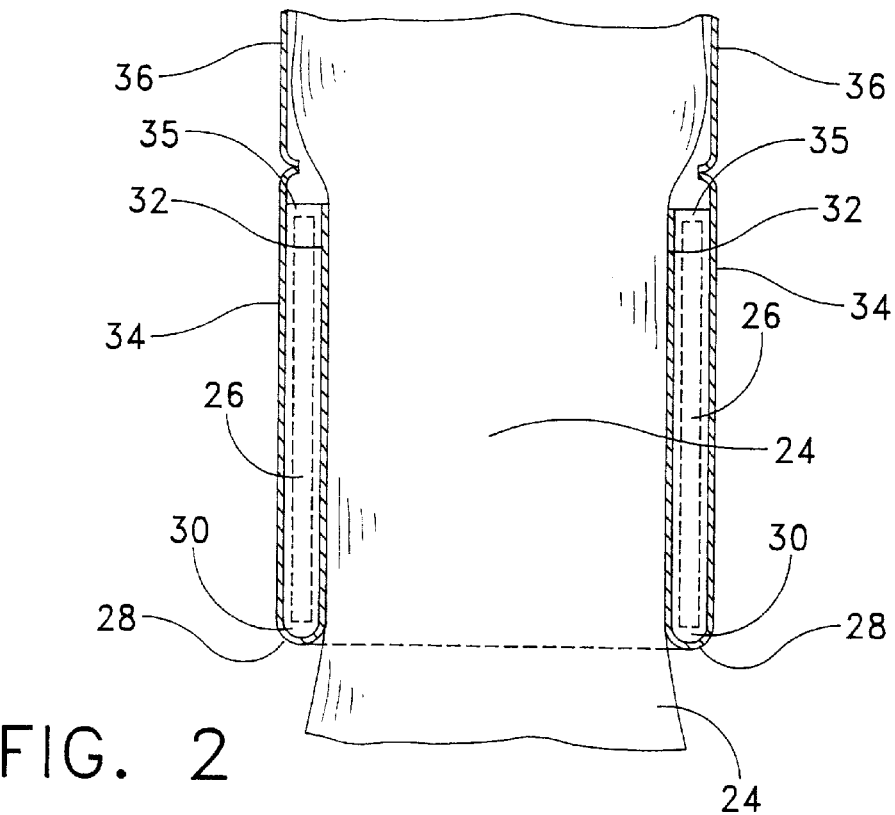
FIG. 2 is a cross-sectional view taken along lines 2—2 of FIG. 1.
Figure 3:
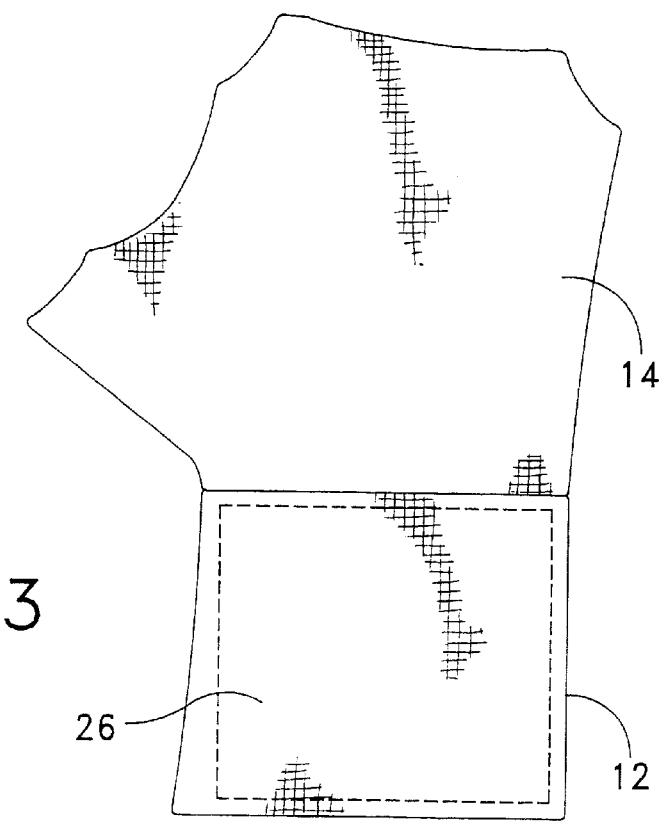
FIG. 3 is a rear view showing a therapeutic pack, in broken lines, received within the inner cuff pocket of the glove.

Referring now to FIGS. 2 and 3, the pocket structure for receiving the selected therapeutic packs 26 in the cuff portion 12 of the glove 10 is more clearly depicted. Specifically, the pockets are formed from an extension of the cuff portion 12 of the glove 10 which is reversely folded over in such a manner at the bottom edge thereof 28 to form pocket cavities 30 at opposing sides of the cuff portion 12 of the glove 10 for receiving the selected therapeutic pack 26. In this connection, it should be understood that the support glove 10 of the instant invention has a generally two part construction, one part covering the front portion of the user's hand 16 and wrist 24, and the other part covering the rear portion of the user's hand 16 and wrist 24. The two part construction is secured together by stitching means which will be described in greater detail as the description hereof proceeds. The pocket structure is defined by opposing inner 32 and outer 34 walls at the interior of the cuff portion 12 of the glove 10. The pockets are left open at their top edge 35 for quick and easy insertion and removal of the selected therapy pack 26 with respect to the cavity 30 of the pocket. Also shown in FIG. 2 is a fragment of opposing wall members 36 which defines the hand portion 14 of the glove 10. As shown, wall members 36 of the hand portion 14 of the glove 10 extend from opposing outer walls 34 which define the cavity 30 of pocket structure of the cuff portion 12 of the glove 10.

Referring now to FIGS. 4–7, the structure of the hand portion 14 of the glove 10 is more clearly depicted. Specifically, the hand portion 14 of the glove 10 is made from a single sheet of spandex-type material and folded over at the terminal end 38 thereof and stitched together at side edges thereof. Specifically, the hand portion 14 of the glove 10 has opposing and identical front and rear walls 36 for covering the back and palm portions of the user's hand 16, respectively. Several openings are provided at the terminal end 38 of the glove 10 through which the user's fingers 18–22 extend when the glove 10 is being worn by the user. Specifically, opening 40 is for the user's thumb 22, opening 42 is for the user's index finger 18, opening 44 is for both the user's ring 20 and middle fingers 19, and opening 46 is for the user's small finger 21. FIG. 5 depicts the opening 48 at the terminal end of the cuff portion 12 of the glove 10 for insertion of the user's hand 16 before the glove 10 is to be worn. The construction of the hand portion 14 of the glove 10 is clearly shown in this view depicting both the front and rear walls 36 secured together at opposing sides of the hand portion 14 of the glove 10. FIGS. 6 and 7 further define the construction of the glove 10, FIG. 6 showing opening 40 through which the user's thumb extends, and opening 42 through which the user's index finger extends. Opening 44 is also depicted through which the user's ring and middle finger extend. The two part construction of the support glove 10 is also illustrated showing front and rear sides of both the hand 14 and cuff 12 portions of the glove 10. FIG. 7 shows opening 46 through which the user's baby or pinky finger extends, and also shows the two part construction of the glove 10 shown in FIG. 6. FIG. 7 also clearly depicts the folded-over one piece nature at the terminal end 38 of the hand portion 14 of the glove 10, and the opening 44 through which the user's ring and middle finger extend.

Figure 8:
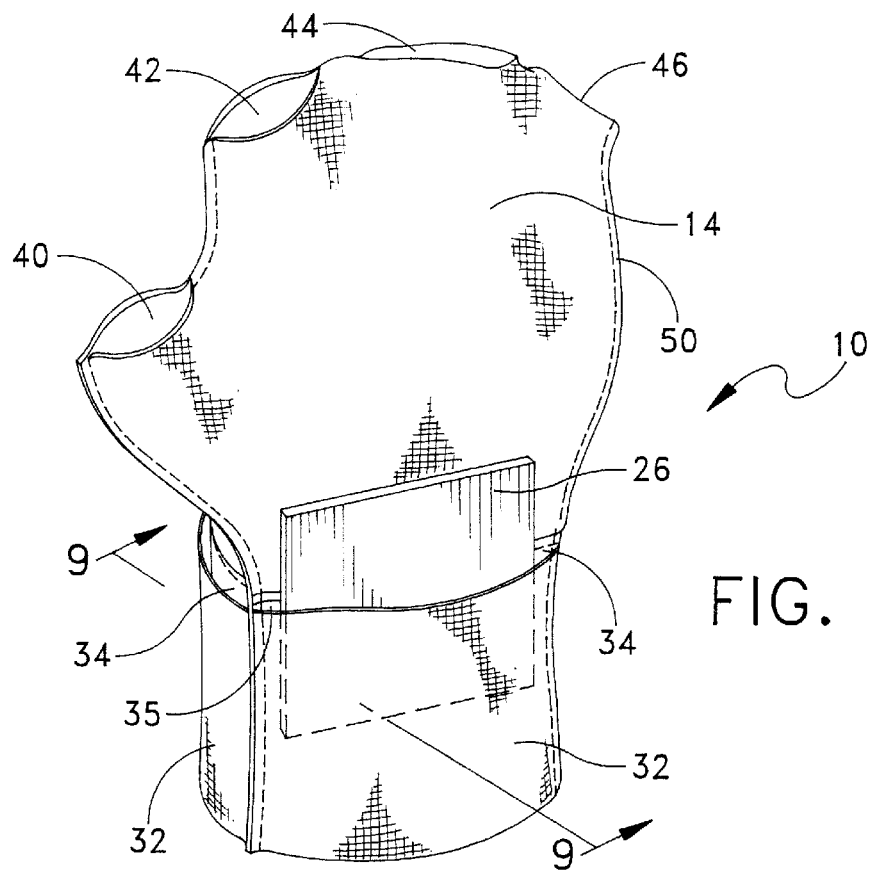
FIG. 8 is a perspective view showing the support glove turned inside out with the therapeutic pack partially inserted in one of the pockets.
Figure 9:
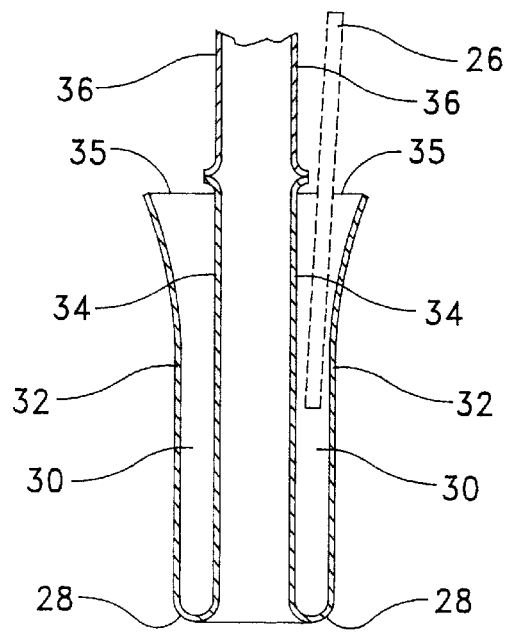
FIG. 9 is a cross-sectional view taken along lines 9—9 of FIG. 8.

Referring to FIGS. 8–11, the therapeutic support glove 10 is shown turned inside out so as to present pockets 30 on the outer surfaces of cuff portion 12. FIG. 8 shows a selected therapeutic pack 26 being inserted into the pocket or cavity 30 on the side of cuff portion 12 that will be adjacent the inside of the user's wrist when the glove is once again returned to its operative position of FIGS. 1–7 and then positioned on the user's hand. Specifically, the glove shown in FIG. 8 will be adapted for wearing on the user's right hand, and when so worn, the pack 26 will be positioned in the pocket adjacent the inside of the user's wrist. It will be understood that the glove as shown in FIG. 8 could be worn on the user's left hand and the pack 26 would be adjacent the inside of the user's wrist, but in such a situation, the pocket 30 would be located on the outer surface of cuff portion 12 which would make it easier for pack 26 to inadvertently become displaced from pocket 30. Thus, positioning the glove in the inside-out position of FIG. 8 is solely to make it easier to insert pack 26 in desired pocket 30. However, once the pack is inserted, the glove is again reversed to once again assume the orientation of FIGS. 1–7 wherein the pocket 30 with pack 26 therein is located on the inside surface of cuff portion 12, which greatly minimizes inadvertent displacement of pack 26 from its pocket 30 while the glove is being worn.

As shown in FIGS. 8–11, the top edge 35 of the pocket cavity 30 is left open for quick and easy insertion and removal of the selected therapeutic pack 26. It should be understood that any number of different therapeutic packs 26 may be inserted into the cavity 30 of the cuff pocket, including heat packs, cold packs, and magnetic packs.

Figure 10:
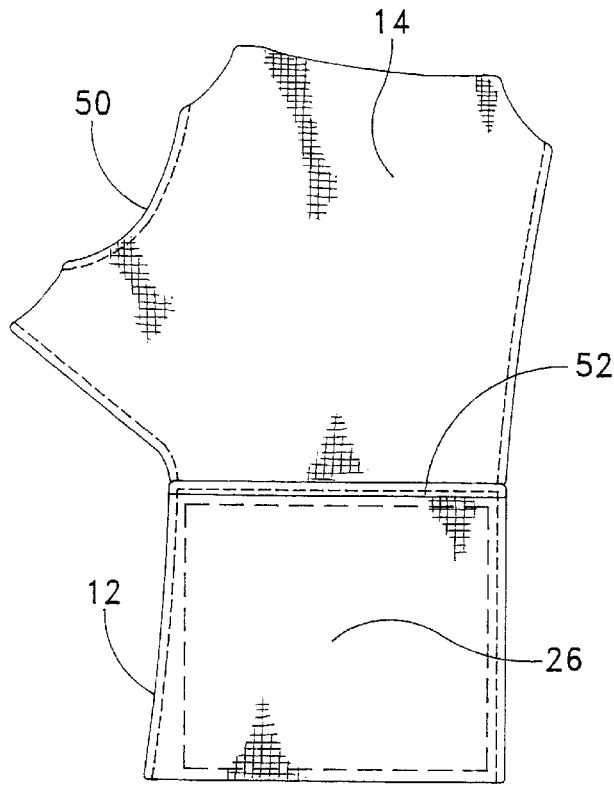
FIG. 10 is a rear view similar to that shown in FIG. 3 showing the support glove turned inside out.
Figure 11:
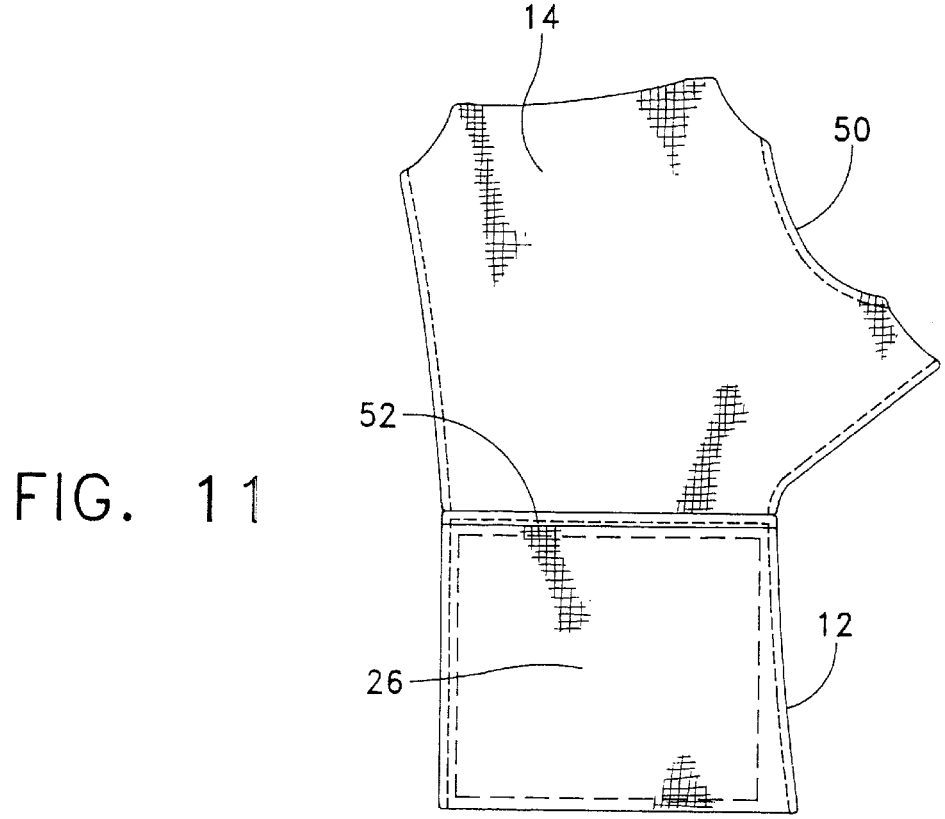
FIG. 11 is a front view showing the support glove turned inside out.

However, it is contemplated that only one such therapeutic pack 26 at a time be inserted into the cavity 30 of the pocket to perform the desired therapeutic process. Also, clearly depicted in FIG. 8 is the stitching seam 50 which extends along the sides of the glove 10 for securing the two part construction of the glove together, i.e., front and rear portions. FIGS. 10 and 11 also depict the glove turned inside out and show the stitching seam 50 extending along the perimeter of both the hand 14 and cuff 12 portions of the glove 10 for maintaining corresponding front and rear portions of the glove 10 sewn together. A further stitching seam 52 runs perpendicularly between stitching seams 50 for securing the cuff portion 12 to the hand portion 14 of the glove 10.

It can therefore be seen that the instant invention provides a therapeutic support glove which is effective for reducing pain resulting from strain, stress, cramping, swelling and associated pain from the fingers, hands and wrist while performing continuous or repetitive hand motion activities. The support glove has a pair of opposing pockets formed in the interior of the cuff portion of the glove for receiving selected therapeutic packs for implementing the desired therapeutical process. The selected therapeutic packs are positioned within the cuff pocket adjacent the inner portion of the user's wrist. The arrangement is such that the therapeutic support glove is interchangeable enabling it to be worn on either of the user's hands while still providing a pocket adjacent the inner portion of the user's wrist. The glove further provides a snug firm fit around the user's hand and leaves the user's fingers uncovered for unrestricted use. For these reasons, the instant invention is believed to represent a significant advancement in the art which has substantial commercial merit.

While there is shown and described herein certain specific structure embodying the invention, it will be manifest to those skilled in the art that various modifications and rearrangements of the parts may be made without departing from the spirit and scope of the underlying inventive concept, and that the same is not limited to the particular forms herein shown and described except insofar as indicated by the scope of the appended claims.

What is claimed is:

1. A therapeutic support glove assembly for providing relief for such things as hand fatigue, carpal tunnel syndrome, arthritis, tendinitis and other known ailments associated with the human hand, said assembly comprising:

a therapeutic pack;

a support glove comprising a cuff adapted to snugly surround a user's wrist, said cuff having two pockets defining corresponding cavities, said pockets positioned in opposing relation to each other so that when said glove is worn on the user's hand, one of said pockets is adjacent the outer portion of the user's wrist, and the other pocket is adjacent the inner portion of the user's wrist, an elongated opening extending along the top edges of said pockets for easy insertion of said therapeutic pack within said pocket cavity, said therapeutic pack positioned adjacent the inner portion of said user's wrist for implementation of the desired therapeutic process; and a hand portion secured to said cuff providing means for covering the inner palm portion and back portion of the user's hand, said hand portion having means formed therein at the end thereof remote from said cuff for receiving the user's fingers when said glove is positioned on the user's hand.

2. The assembly of claim 1 further characterized in that the means for receiving the user's fingers comprise openings at the end of said hand portion remote from said cuff, whereby the user's fingers are adapted to extend through said openings and remain uncovered and unrestricted when the glove is in use.

3. The assembly of claim 1 further characterized in that said support glove is made from a spandex-like material.

4. The assembly of claim 1 further characterized in that said pockets are located on the inside surface of said cuff.

5. A therapeutic support glove comprising:

a cuff adapted to snugly surround a user's wrist, said cuff having two pockets defining corresponding cavities, said pockets positioned in opposing relation to each other so that when said glove is worn on the user's hand, one of said pockets is adjacent the outer portion of the user's wrist, and the other pocket is adjacent the inner portion of the user's wrist, an elongated opening extending along the top edges of said pockets whereby said pockets are adapted to readily receive therein a selected therapeutic pack;

a hand portion secured to said cuff providing means for covering the inner palm portion and the back portion of a user's hand, said hand portion having means formed therein at the end thereof remote from said cuff for receiving a user's fingers.

6. The support glove of claim 5 further characterized in that the means for receiving the user's fingers comprise openings at the end of said hand portion remote from said cuff, whereby the user's fingers are adapted to extend through said openings and remain uncovered and unrestricted when the glove is in use.

7. The support glove of claim 5 further characterized in that said support glove is made from a spandex-like material.

8. The support glove of claim 5 further characterized in that said pockets are located on the inside surface of said cuff.

* * * * *

UNITED STATES PATENT AND TRADEMARK OFFICE
CERTIFICATE OF CORRECTION

PATENT NO. : 6,029,277
DATED : February 29, 2000
INVENTOR(S) : Nicholas Picchione, II It is certified that error appears in the above-identified patent and that said Letters Patent is hereby corrected as shown below:

On the title page: Item [73] Assignee: should read
--Data Binding, Inc. --.

Signed and Sealed this

Ninth Day of January, 2001

Attest:

Q. TODD DICKINSON

*Attesting Officer*      *Commissioner of Patents and Trademarks*